US005327081A

United States Patent [19]
Rudd et al.

[11] Patent Number: 5,327,081
[45] Date of Patent: Jul. 5, 1994

[54] METHOD FOR DETERMINING THE THICKNESS OF A MATERIAL BY MEANS OF A RADIANT ENERGY PROBE

[75] Inventors: George E. Rudd, Murrysville; Rajender K. Sadhir, Pittsburgh; William G. Clark, Jr., Murrysville Boro; Robert E. Shannon, Export, all of Pa.

[73] Assignee: Westinghouse Electric Corporation, Pittsburgh, Pa.

[21] Appl. No.: 68,311

[22] Filed: May 28, 1993

Related U.S. Application Data

[63] Continuation of Ser. No. 668,838, Mar. 31, 1991, abandoned.

[51] Int. Cl.$^5$ .............. G01B 7/10; G01N 27/90; G01R 33/12; G01R 35/00
[52] U.S. Cl. .................... 324/230; 324/202
[58] Field of Search ............ 324/229, 230, 202, 231, 324/214

[56] References Cited

U.S. PATENT DOCUMENTS

| | | | |
|---|---|---|---|
| 2,862,178 | 11/1958 | Moore | 324/202 |
| 3,420,923 | 1/1969 | Ashworth et al. | |
| 3,427,264 | 2/1969 | Forster et al. | |
| 4,003,840 | 1/1977 | Ishino et al. | 252/62 |
| 4,024,318 | 5/1977 | Forster et al. | 428/519 |
| 4,700,486 | 10/1987 | Puumalainen | 33/147 L |
| 4,727,322 | 2/1988 | Lonchampt et al. | 324/229 |
| 4,762,864 | 8/1988 | Goel et al. | 523/428 |
| 4,767,987 | 8/1988 | Montgomery | 324/231 |
| 4,774,265 | 9/1988 | Ugelstad et al. | 521/55 |
| 4,803,428 | 2/1989 | Crostack | 324/202 |
| 4,814,703 | 3/1989 | Carr et al. | 324/229 |
| 4,849,020 | 7/1989 | Osborne et al. | 106/281.1 |
| 4,870,359 | 9/1989 | Takahashi | 324/229 |
| 4,940,633 | 7/1990 | Hermansen et al. | 428/324 |
| 4,944,185 | 7/1990 | Clark, Jr., et al. | 73/579 |
| 5,017,869 | 5/1991 | Oliver | 324/230 |

OTHER PUBLICATIONS

Article appearing in *Internation Science & Technology*, Entitled "Magnetic Fluids", Jul. 1966.
Article appearing in *Westinghouse Technology*, Entitled "Tagged Materials 'Speak' for Themselves", Winter 1990.
Article appearing in *ENR* Entitled "Vibrating Iron Particles to Sound Out Problems", Jul. 13, 1989.
Article appearing in *Engineering Times*, Entitled "Embedded Iron Dust Reveals Inner Secrets of Concrete", Aug. 1989.
Article appearing in *Science News*, vol. 135, Entitled "Making Concrete, Smarter than it Looks", May 6, 1989.

(List continued on next page.)

*Primary Examiner*—Hezron E. Williams
*Assistant Examiner*—Nashmiya N. Ashraf

[57] ABSTRACT

A nondestructive method for determining the thickness of a non-electrically conductive material is provided that comprises the steps of uniformly dispersing a quantity of a ferromagnetic particulate tagging substance in the material whose presence and distribution is detectable by a form of radiant energy, such as the high-frequency electromagnetic field emanated from an eddy current probe, and then calibrating the output of the eddy current probe with a sample material having a known thickness that has been tagged with the same tagging substance at the same density. The thickness of the material is then determined by comparing the amplitude of electromagnetic coupling with the material with that obtained with the sample. The method may advantageously be applied to determine the thickness of a granular material such as asphalt concrete over a roadbed, as well as the strain and wear patterns in gaskets formed from elastic materials.

9 Claims, 6 Drawing Sheets

OTHER PUBLICATIONS

Article appearing in *Concrete International*, Entitled "Tagging Technology", Sep. 1989.

Article appearing in *Civil Engineering*, Entitled "Researchers Embed Tags to Test Materials", Aug. 1989.

Article appearing in *The Military Engineer*, No. 531, Entitled "Tagging Materials for Improved Inspection", Sep.-Oct. 1989.

Article appearing in *The Wall Street Journal*, Entitled "Westinghouse's Electromagnetic 'Tags' May Detect Flaws in Buildings, Roads", Jun. 12, 1989.

Article appearing in the *Pittsburgh Post Gazette*, Entitled "A New Eye on Quality", Aug. 28, 1989.

Article appearing in *The Construction Specifier*, Entitled "New Tagging Technology Could Mean Better Structures", Aug. 1989.

Article appearing in *High Technology Business*, Entitled "New Developments", Sep.-Oct. 1989.

Article entitled "Tagged Adhesives for Improved Electromagnetic Inspection", appearing in *Materials Evaluation* Jan. 1990 By W. G. Clark, Jr., R. K. Sadhir and W. R. Junker.

Article entitled "Tagging Lets You Test the Untestable", appearing in Advanced Materials & Process; Apr. 1990, By W. G. Clark, Jr., and R. E. Shannon.

Article entitled "Iron Test for Concrete" appearing in *Financial Times*, Jun. 1989.

METHOD FOR DETERMINING THE THICKNESS OF A MATERIAL BY MEANS OF A RADIANT ENERGY PROBE

This application is a continuation of Ser. No. 07/668,838, filed Mar. 31, 1991, now abandoned.

BACKGROUND OF THE INVENTION

This invention relates to a method for determining the amount of deformation induced in a material in response to a compressive force. The invention may be used to determine the extent and uniformity of asphalt compaction in a road building operation, or the stress patterns present in a gasket formed from elastomeric material.

Methods for determining the extent to which a material is deformed in response to a compressive force are known in the prior art. Such methods find application in fields as varied as road construction and in tests for determining the ability of compressed gasket to maintain a fluid-tight seal. In the case of road construction, these methods perform the important function of indicating whether or not the granular asphalt that is compressed by a steam roller over a roadbed has been effectively compacted into a road structure having a uniform asphalt density and thickness over its surface, as nonuniformities in thickness and density result in a road that is undesirably uneven and that might include void spaces. Such unevenness and void spaces can result in rutting, and can also collect water within the road structure that can turn into ice and create pot holes. In the case of gaskets, such method are used to estimate the uniformity and the intensity of the strain imposed on the gasket material by the bolts or other structures which serve to compress the gasket between two surfaces to create a sealing interface. Such knowledge of the strain patterns can in turn be used to estimate the effectiveness of the resulting seal, and even the expected wear pattern and life expectancy of the gasket.

Unfortunately, there are a number of shortcomings associated with the testing methods used in the prior art which significantly undermine their usefulness. For example, in the case of roadmaking, the compaction and thickness of the granular asphalt used to build the road may be estimated by extracting a number of random core samples over the newly constructed road. Needless to say, such a sampling technique destructively creates holes in the new road's surface which need to be repaired. Additionally, such testing may well fail to inform the road builders of the existence of one or more faulty areas in the road structure, since the information relied upon is confined to only a few randomly taken samples. Of course, the relative accuracy of such prior art testing could be improved by taking a larger number of samples. However, more extensive sampling would involve a concomitant increase in the damage to the road, and the time and expense associated with such testing. To avoid the problem associated with testing based upon core sampling, testing techniques based upon the irradiation of the road with a neutron source are also known. In such tests, the density of the asphalt is determined by measuring the amount and types of secondary radiation that results from the initial neutron radiation. However, such testing requires the use of expensive equipment and skilled operators, and utilizes potentially hazardous radiation. Also, since this testing can only be performed on a sampling basis, it is possible that large faults in the road may be missed.

In the case of gaskets, there are no known, direct nondestructive testing procedures which would allow one to accurately determine the strain patterns that result in such a gasket as a result of the compressive forces applied to it by the surrounding clamping structure. However, since it is known that the compressive load applied over the gasket should be as uniform as possible to avoid the development of premature leaks in the resulting gasket seal, attempts are routinely made to apply as uniform a clamping force as possible between the gasket and the surfaces that it seals. For example, where this clamping force is applied by a plurality of bolts, the person installing the gasket may attempt to equilibrate the compressive load on the gasket by applying an equal amount of torque on each bolt. Unfortunately, because there are many variables in the relationship between the amount of torque applied to a bolt and the resulting compression (such as thread imperfections, the presence of dirt or lubrication in the threads, etc.) the application of equal amounts of torque on the bolts may not result in a corresponding pattern of equal strain on the gasket.

Clearly, there is a need for a nondestructive method that accurately and reliably determines the amount of deformation induced in a material in response to a compressive load. Ideally, such a method would be able to determine the amount of compressive present in the material over the entire surface of the material, rather than a relatively few, isolated sample points so that the presence or absence of significant areas of nonuniformity in the deformation could be easily detected and corrected. It would further be desirable if such a method could be quickly and reliably applied to both large open surfaces, such as an asphalt road under construction, as well as to small surfaces of relatively difficult accessibility, such as an operational gasket compressed between two opposing surfaces. Finally, it would be desirable if such a test were not confined to only a few specialized materials, but was universally applicable to a broad spectrum of materials used not only in road building or gaskets, but virtually any engineering application that involved the application of a compressive force to a material.

SUMMARY OF THE INVENTION

Generally speaking, the invention is a method for nondestructively determining the thickness of a structure formed of a non-electrically conductive material that is adjacent to a second material that is both non-electrically conductive an non-ferromagnetic by means of an eddy current probe. The invention may also be use for nondestructively determining the amount of deformation induced in a material by a compressive force which overcomes or at least ameliorates the shortcomings associated with the prior art. The method comprises the steps of uniformly dispersing a quantity of a particulate tagging substance in the material whose presence and distribution is detectable by some form of radiant energy; applying a compressive force to the material, and determining the extent to which the material is compressively deformed by the force by transmitting the appropriate form of radiant energy through the material to determine changes in the density and distribution of the particulate tagging substance.

The material may either be a solid material that elastically deforms in response to a compressive force of a certain magnitude and then inelastically deforms in response to a force having a greater magnitude, or the material may be a particulate, compactable material having air spaces between the particles which are reduced in size when the material is compressed. The particulate tagging substance may be formed from a ferromagnetic material that interacts with either microwaves or an alternating magnetic field, or these particles may be formed from a substance such as quartz that changes the acoustical impedance of the material, or its optical properties. In the latter two cases, the radiant energy employed to detect the density and distribution of the particles may be either ultrasound, or light. In many instances, the radiant energy used to detect the density and distribution of the tagging particles is applied along the same direction as the compressive force so that variations in the amount of deformation occurring over an area of the material can be readily detected.

The invention encompasses a method of determining the extent to which an asphalt concrete is compacted over a supporting surface, such as a roadbed, wherein a quantity of particulate ferromagnetic material is mixed throughout the volume of the rocky material in the asphalt concrete, and the asphalt concrete is compressed over the supporting surface in order to compact it into a solid structure such as a road. The uniformity of the compaction of the asphalt concrete may be determined by first applying radiant energy to it in the form of microwaves that couple with the ferromagnetic particles in the rocky material and cause the entire asphalt structure to heat up, and then by thermally scanning the upper surface of the compacted asphalt with an area heat sensor in order to detect the presence or absence of temperature gradients in the asphalt. An isothermic heating of the asphalt would indicate a uniform compaction of the asphalt, whereas the presence of significant temperature gradients would indicate voids or areas of greater and lesser compaction. Alternatively, the extent to which such asphalt concrete is uniformly compacted by the compressive force may be determined by an eddy current probe which transmits a fluctuating electromagnetic field through the compacted asphalt which electromagnetically couples with the ferromagnetic particles uniformly distributed in the rocky material therein. Any non-uniformities in the amount of electromagnetic coupling would again indicate the presence of undesirable voids or areas of loose compaction.

The invention also advantageously encompasses a method for determining both the strain pattern and wear pattern in a gasket formed from an elastic material. In this embodiment of the method, a particulate tagging substance, which may take the form of fine ferromagnetic particles, is uniformly dispersed in the material forming the gasket. Such particles may be uniformly dispersed throughout the volume of the material forming the gasket, or they may be dispersed only on its outer surfaces. After a compressive force is applied to the gasket, the outer surface of the gasket is scanned by means of a fluctuating electromagnetic field emanated by for example an eddy current probe in order to determine variations in the density and distribution of the ferromagnetic particles in the gasket material. This method may further include the step of repeating the scanning of the gasket by the fluctuating electromagnetic field after the gasket has been put into operation in order to determine areas of wear or any cracks or faults which may have occurred within the gasket during its operation.

In all cases, the method of the invention is simple and inexpensive to implement, and is capable of quickly providing reliable and accurate information regarding compressive deformation throughout every point on the structure being inspected in a variety of materials without the need for time consuming and potentially inaccurate random sampling or of destructive testing.

DETAILED DESCRIPTION OF THE PREFERRED EMBODIMENT

Figure 1A:
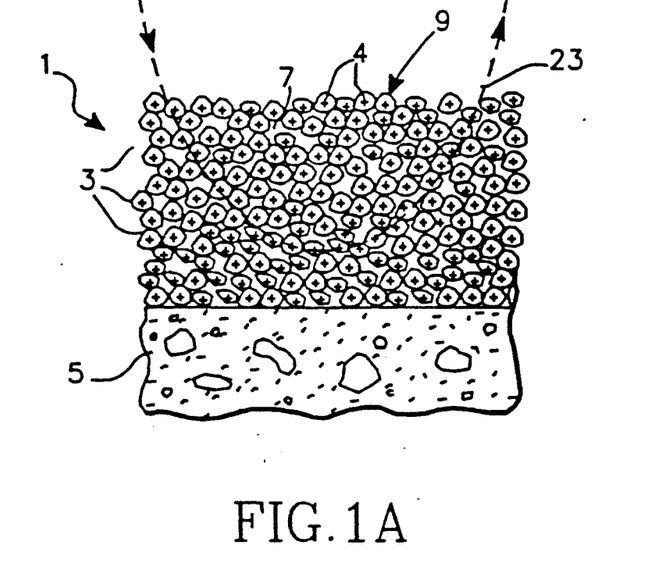
FIG. 1A is a cross-sectional side view of a road being built with uncompacted asphalt concrete that has been impregnated with ferromagnetic tagging particles.
Figure 1B:
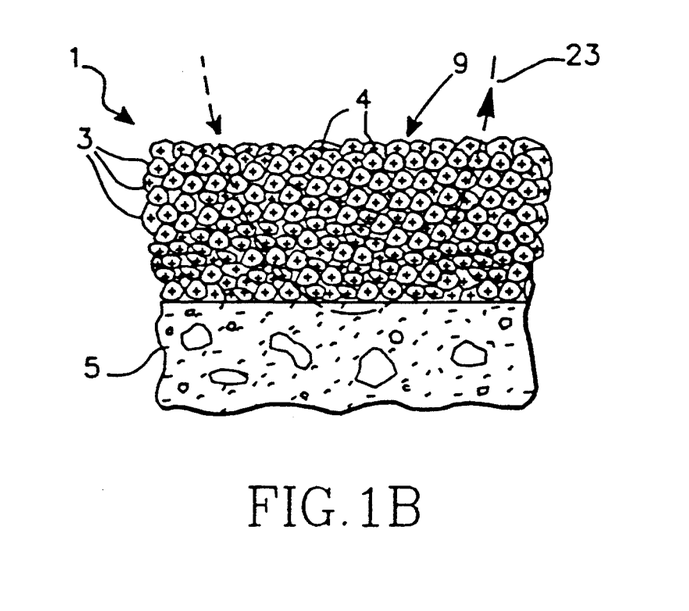
FIG. 1B illustrates how the compaction of the asphalt concrete illustrated in FIG. 1A results in denser distribution of the ferromagnetic tagging particles contained within the asphalt to the lines of magnetic flux emanated by an eddy current probe assembly.

FIGS. 1A and 1B illustrate how the method of the invention can be advantageously used to inspect a newly-constructed road 1 for faults. Such roads are formed by the application and compaction of asphalt formed from a mixture of rocky granules 3 mixed with a tarry binder. In this example of the method of the invention, each of the rocky granules 3 has been impregnated with ferromagnetic tagging particles 4. While it is possible to obtain the advantages of the invention with asphalt wherein only the surfaces of the granules 3 have been impregnated with ferromagnetic tagging particles 4, each of the rocky granules 3 is preferably impregnated with such particles 4 completely throughout its volume in this particular example of the method. While there is no set amount of ferromagnetic tagging particles that must be uniformly dispersed throughout the asphalt concrete to allow the method of the invention to be implemented, a mixture of between 0.5 and 10.0 weight percent of such particles is preferred, and a mixture of between about 1.0 and 3.0 weight percent is even more preferred. To this end, an aqueous colloidal solution of ferromagnetic iron ligansulfonate (sold under the trademark Lignosite ® may be impregnated throughout the rocky granules 3 of the asphalt.

In the construction of such roads 1, a loose mixture of rocky granules 3 and tarry binder is first applied over a roadbed 5, as is illustrated in FIG. 1A. Such loosely deposited granules 3 include a large number of air spaces 7 inbetween the individual granules 3. If allowed to remain, such air spaces 7 would not only seriously derogate the integrity of the asphalt structure by causing "rutting" to occur in the road whenever the wheels of a heavy truck ran over the road; they would also create a situs where water can collect, freeze and expand, thereby creating unwanted potholes. Accordingly, it is standard practice to apply a compacting force to such asphalt granules 3 by means of a steamroller or the like not only to substantially eliminate all the air spaces 7, but further to create a relatively smooth upper surface 9 on the road 1.

The compaction of the rocky granules 3 of the asphalt concrete into the relatively void-free configuration illustrated in FIG. 1 has the effect of increasing the density of the ferromagnetic tagging particles 4, as well as defining a much smoother upper surface 9. After such a compacting force has been applied to the rocky granules 3, the method of the invention may be implemented by means of the eddy current probe assembly 11 illustrated in perspective in FIG. 2. In this example, the probe assembly 11 includes an array of independently actuatable, concentric sensing coils 13 ranging between three inches and two feet in diameter. The coils 13 are contained within a housing 15 which in turn in mounted on a platform 17 supported by wheels 19 at each corner. A handle assembly 21 is provided to allow the operator of the eddy current probe assembly 11 to completely scan the newly constructed asphalt road 1 by manually pushing the assembly 11 over the road 1 in the same way that a lawn mower is pushed over all the surface of a yard. Although not specifically shown in FIG. 2, the various-diametered sensing coils 13 are each independently connected to commercially-available eddy current circuitry, such as a MIZ-18 multifrequency generator manufactured by Zetec located in Isaquah, Washington. Such a multifrequency generator is capable of applying alternating current having a plurality of different frequencies to the various sensing coils 13 contained within the housing 15 of the assembly 11, which in turn results in the generation of a plurality of different fluctuating magnetic fields which are capable of penetrating the asphalt road 1 to a greater or lesser degree. For a detailed description of the advantages associated with the use of such independent, concentrically arranged probe coils, reference is made to U.S. Pat. No. 4,855,677 by Clark, Jr. et al. and assigned to the Westinghouse Electric Corporation, the entire specification of which is expressly incorporated herein by reference.

Figure 2:
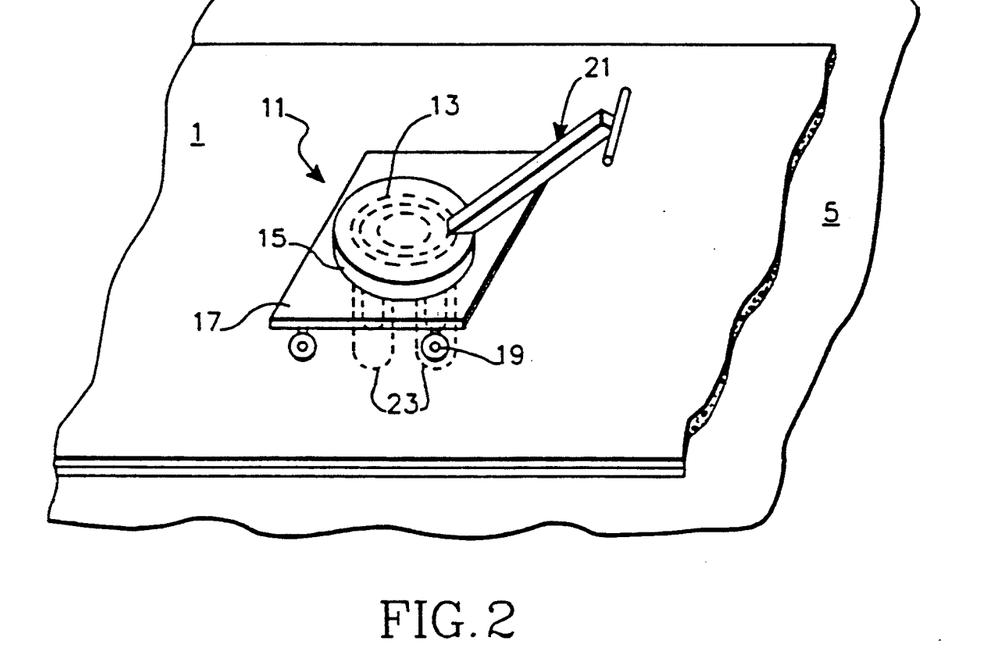
FIG. 2 is a perspective view illustrating how a manually pushed eddy current probe assembly may be used to implement the method of the invention to scanning a newly-compacted road in order to determine whether or not the asphalt forming the road has been compacted to a desired thickness and density.

In the first step of this example of the method of the invention, the eddy current probe 11 is calibrated by rolling it over a sample road which conforms to all structural specifications, and in which the rocky granules 3 in the asphalt concrete have been impregnated with the same percentage and type of ferromagnetic tagging particles 4. The eddy current circuitry ( not shown ) is operated at a plurality of different frequencies in order to generate a corresponding number of fluctuating electromagnetic fields 23, some of which interact primarily with the upper surface 9 of the road 1, and others of which will interact with the entire thickness of the road 1. The magnitude of the amount of electromagnetic coupling that occurs between these various alternating electromagnetic fields and the ferromagnetic particles 4 contained within the compacted rocky granules 3 in the calibration sample are carefully noted for each coil and for each frequency of alternating current, and stored in the memory of a microprocessor (not shown), such that the microprocessor "knows" precisely what kind of signal strengths to expect for a road made of asphalt that has been compacted to a desired density and built up to a desired thickness.

After the calibration step has been completed, the eddy current probe assembly 11 is carefully rolled over the upper surface 9 of the newly constructed road 1 in order to scan each square unit of the road 1 with the fluctuating electromagnetic fields emanated by the sensing coils 13. The strength of the coupling that takes place between these fields and the electromagnetic tagging particles 4 in the asphalt 3 is recorded in the memory of the microprocessor, and then compared to the information acquired during the calibration step. Any areas of the asphalt road 1 which do not exhibit electromagnetic coupling characteristics consistent with the sample road used to calibrate the probe assembly 11 are earmarked as by, for example, fluorescent road cones . After the inspection has been complete, corrective action is taken on any parts of the newly constructed road 1 which did not pass inspection.

Figure 3:
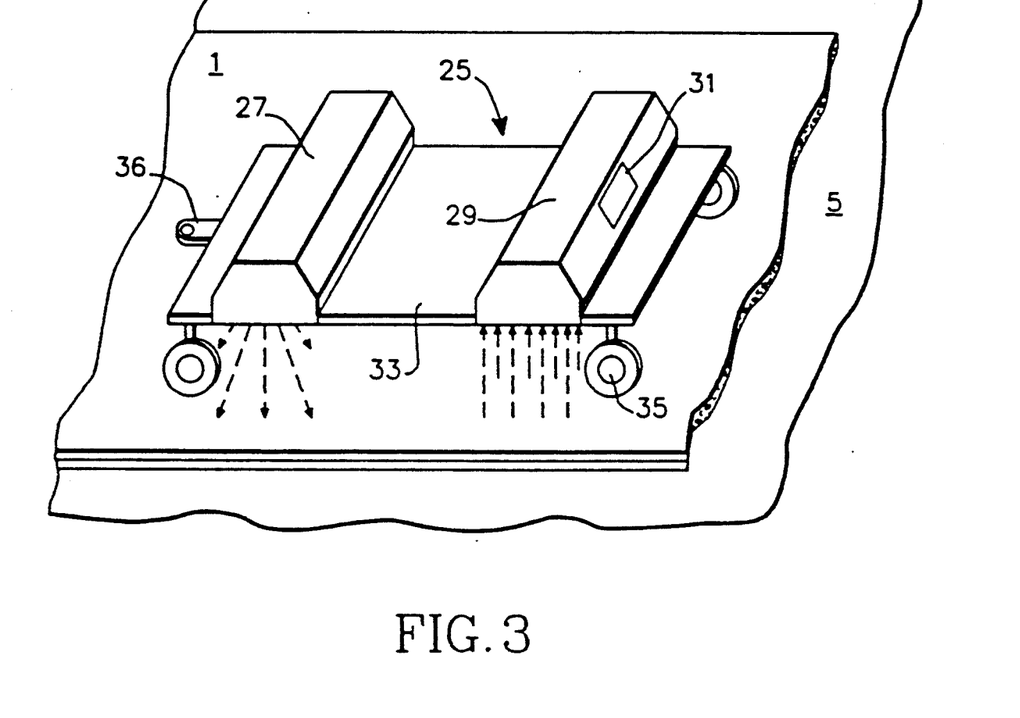
FIG. 3 is a perspective view of a thermal scanner assembly which may be used to implement the method of the invention by first heating a newly compacted road with microwave energy and then thermally scanning the heated road in order to determine whether or not the asphalt forming the road has been compacted to a desired thickness and density.

FIG. 3 illustrates how an alternate embodiment of the method of the invention might be implemented. In this particular embodiment of the method, the density and thickness inspection of the asphalt road 1 is performed by means of a thermal scanner assembly 25. This particular embodiment of the method takes advantage of the fact that ferromagnetic tagging particles not only interact strongly with the high frequency, fluctuating electromagnetic fields emanated by eddy current probes; they further respond to exposure to microwave radiation by heating up. As the heat radiation characteristics of such tagged granules 3 of asphalt are dependent upon both the density and the thickness of the ferromagnetic particles in the asphalt structure, such a thermal scanner assembly 25 affords an alternate means of inspecting a newly constructed asphalt road 1 for structural faults.

To this end, the thermal scanner assembly includes the previously mentioned microwave source 27, as well as an area thermal scanner 29 having a readout screen 31. The area thermal scanner 29 may be constructed a number of different ways, as for example by an array of infrared-sensitive semiconductor devices whose collective output is capable of tracing heat gradients across an area being scanned. Both the microwave source 27 and area thermal scanner 29 are mounted in tandem on a carriage 33 rotatably supported by a set of four wheels 35 on the corners of the carriage 33. A trailer hitch 36 located on the front of the carriage 33 allows the carriage 33 to be conveniently pulled over the newly constructed road 1 by motorized vehicle.

In the first step of this particular embodiment of the method of the invention, the thermal scanner assembly 25 is calibrated by operating it over a sample section of asphalt road 1 that conforms to desired thickness and compaction specifications, and which has been tagged with the same percentage of ferromagnetic tagging particles 4. While any one of a number of different frequencies of microwaves might successfully be employed by the thermal scanner assembly 25, a microwave frequency that is associated with a maximum amount of variation in the heat radiative characteristics between a road having desirable structural characteristics versus a road having undesirable structural characteristics is chosen.

The calibration step for the thermal scanner assembly 25 is carried out in much the same fashion as the calibration step associated with the previously described eddy current probe assembly 11, i.e., the heat radiative properties of the asphalt concrete in the sample road 1 which conforms to desired density and thickness specifications are carefully taken note of and recorded in the memory of a microprocessor (not shown). In the subsequent steps of this particular embodiment of the method, both the microwave source 27 and area thermal scanner 29 are activated, and the thermal scanner assembly 25 is methodically rolled over the newly constructed road 1 in a scanning pattern while the microprocessor compares the heat radiative characteristics of the tagged asphalt 3 forming the road 1 with the calibration example stored in its memory. Areas of the newly constructed road 1 which depart from the heat radiative characteristics associated with a properly constructed road are again earmarked by, for example, fluorescent road cones. The last step of the method of the invention, corrective action is taken toward any area of the road which fails to pass inspection.

Figure 4A:
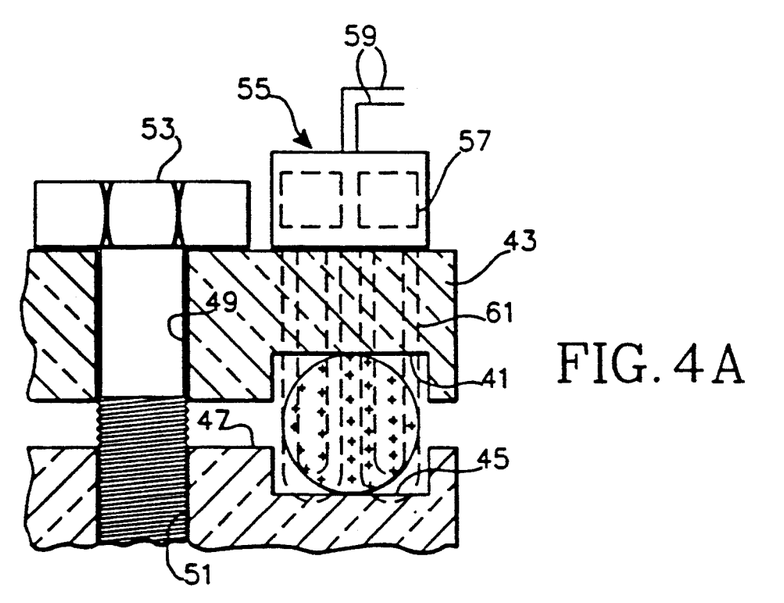
FIG. 4A is a cross-sectional side view of an O-ring gasket that has been tagged with ferromagnetic particles as it would appear in an uncompressed state between a cap and the upper edge of a pressurized vessel.
Figure 4B:
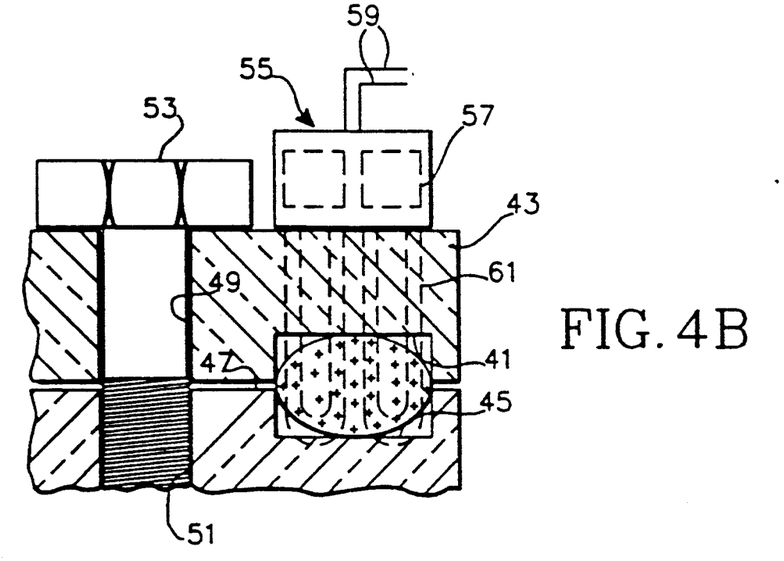
FIG. 4B illustrates how the O-ring illustrated in FIG. 4A appears when compressed and how an eddy current probe may be used to implement the method of the invention by detecting changes in the distribution of the ferromagnetic particles embedded within the material forming the O-ring.

With reference now to FIGS. 4A and 4B, the method of the invention may also be used to determine the amount of deformation induced in an O-ring 37 that has been tagged with ferromagnetic particles 39. In this particular example, the O-ring 37 is captured between a recess 41 located within the periphery of a cap 43, and a recess 45 located around the upper edge 47 of a pressurized container. The cap 43 includes a smooth bore 49 which is registrable with a threaded bore 51 located in the upper edge 47. A bolt 53 is insertable through the smooth bore 49 and engageable with the threaded bore 51 to apply a clamping pressure between the cap 43, and the upper edge 47 of the container.

FIG. 4B illustrates how the O-ring 37 is deformed into pressure-sealing contact within the recesses 41,45 located within the cap 43, and upper edge 47 of the container. As is plainly evident in FIGS. 4A and 4B, the deformation of the O-ring 37 from a circular cross-section to an ovular one when the bolt 53 is wrung up creates a change in the relative distribution and density of the ferromagnetic tagging particles 39 contained within the O-ring 37. These changes in density and distribution may be detected by means of an eddy current probe 55 having a sensing coil 57 that includes leads 59 that are connectable to eddy current circuitry such as the previously described multifrequency generator. The frequency of the alternating current conducted through the sensing coil 57 is adjusted so that the lines 61 of magnetic flux generated thereby strongly interact across the cross-section of the O-ring 37 as shown. The eddy current probe 55 may be used to implement the method of the invention by sensing how the density of the ferromagnetic particles 39 in the O-ring 37 diminishes throughout the center part of the O-ring and increases toward its sides as the bolt 53 is turned to apply a compressive force to the O-ring 37. In this particular example of the method, the eddy current probe 55 is scanned around the periphery of the cap 43 just above the O-ring 37 to determine not only the amount that the O-ring 37 has been deformed into an ovular cross-section as shown in FIG. 4B, but also the uniformity of this deformation.

Ideally, the O-ring 37 should be deformed just enough across each section of its length to ensure the desired level of fluid-type seal, but no more, as excessive deformation creates areas of premature wear that can ultimately result in leaks. If the method of the invention is conducted at the time when the cap 43 is secured over the upper edge 47 of the pressure tight container, the information obtained from the eddy current probe 55 may be used to tighten or loosen the bolts 53 such that the desired pattern of uniform ovular deformation is obtained at each point of the circumference of the O-ring 37. In cases where the O-ring 37 to be inspected has already been mounted in place, the eddy current probe 55 may be used to determine the extent of the cross-sectional deformation of the O-ring and any non-uniformities in such deformation, but also whether or not the O-ring has developed any cracks or other discontinuities which could interfere with its ability to hold a seal.

While the cap 43 and upper edge 47 of the container are shown in FIGS. 4A and 4B to be formed from plastic, it can also be formed from a conductive material such as steel or other metals without impairing the ability of the eddy current probe 55 to extract the desired information from the tagged O-ring 37. However, in a case where the O-ring 37 is surrounded by metals or other conductive materials, it may be necessary to impregnate the O-ring 37 with a material whose electromagnetic coupling characteristics are substantially different from the coupling characteristics from the surrounding structures. Also, while the eddy current probe 55 is illustrated as being oriented such that the lines of magnetic flux 61 which it emanates are substantially parallel to the direction of the clamping force applied by the bolt 53, this particular embodiment of the method will equally well if the sensing coil 57 of the probe 55 were oriented 90 degrees with respect to the position shown in these figures, which would place it over the gap between the outer edge of the cap 43 and the upper edge 47 of the pressurized container.

Figure 5:
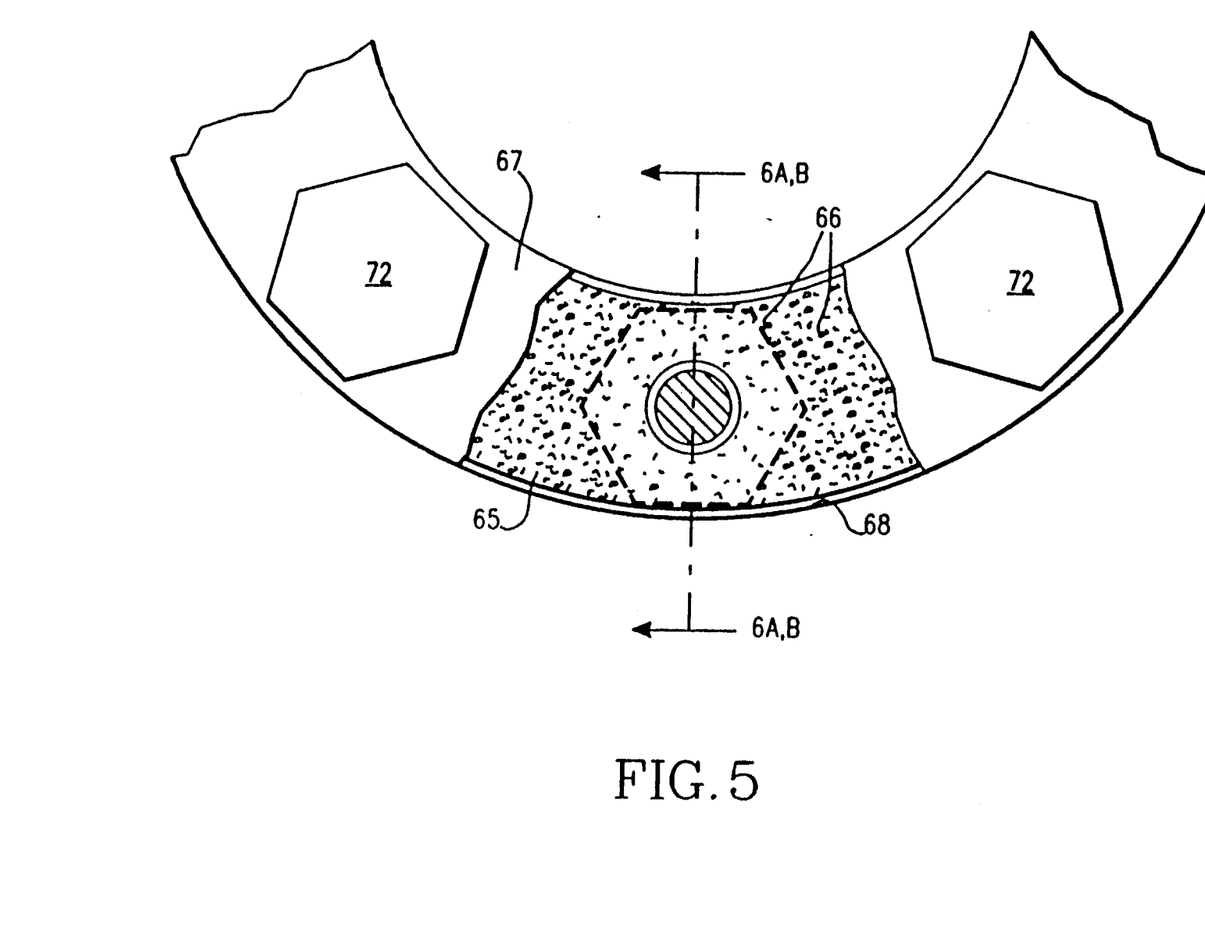
FIG. 5 is a partial plan sectional view of a gasket compressed between a sealing ring and the upper edge of a container illustrating how the strain created in the gasket around the vicinity of a sealing bolt by means of an eddy current probe when Just the surface of such a gasket is impregnated with ferromagnetic particles.
Figure 6A:
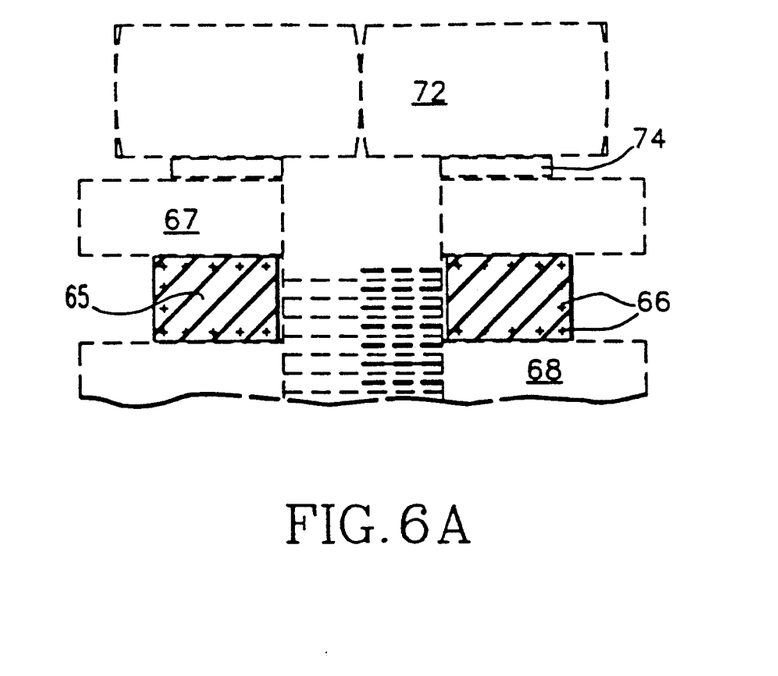
FIG. 6A is a cross-sectional side view of the annular gasket illustrated in FIG. 5 along the line 6A,B–6A,B illustrating how the distribution of the ferromagnetic particles impregnated in the surface of the gasket would appear when the gasket is in an uncompressed state.
Figure 6B:
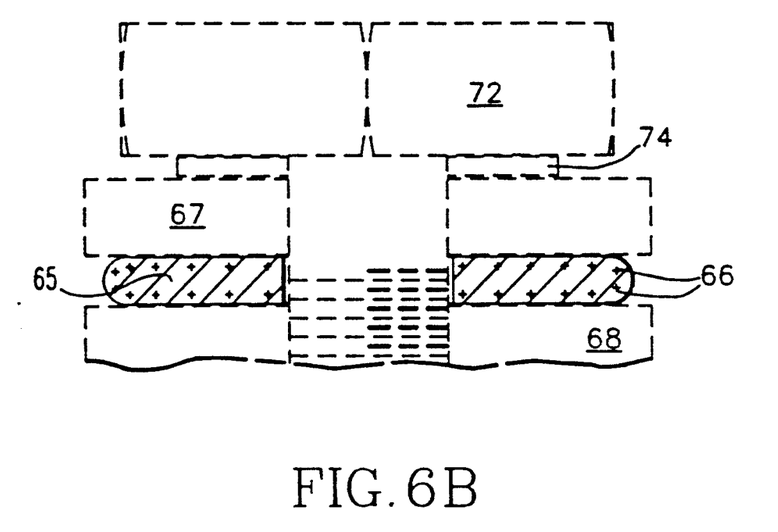
FIG. 6B illustrates how the density and distribution of the ferromagnetic particles in the annular gasket illustrated in FIG. 5 and 6A changes in the vicinity of a bolt which applies a local compressive force to the gasket.

FIGS. 5, 6A and 6B illustrate how the method of the invention may be used to determine the local strain patterns in a flat, annular gasket 65. In this example, the gasket 65 has been impregnated with ferromagnetic particles only on its outer surfaces, as the provision of such particles 66 completely throughout the volume of the gasket 65 is unnecessary. In this particular example, the annular gasket 65 is captured between a compression ring 67 and the upper edge 68 of a pressurized container. The ring 67, the container 68 and the gasket 65 are all provided with mutually registering bores 70 for receiving a plurality of bolts 72 which are uniformly spaced around the compression ring 67 in order to clamp the gasket 65 into sealing engagement between the ring 67 and upper edge 68 of the container. Washers 74 are provided between the clamping bolts 62 and the upper surface of the compression ring 67.

FIG. 6A illustrates how the cross-section of the gasket 65 appears in its uncompressed state. Note the uniform density of the tagged particles 66 around the outer surface of the ring 65. By contrast, FIG. 6B illustrates how the cross section of the gasket 65 changes upon the application of a clamping force by the clamping bolts 72, which react upon the upper surface of the gasket 65 through the washer 74, and the compression ring 67. As is evident from both FIGS. 5 and 6B, the localized nature of the clamping pressure generated by the clamping bolts 72 creates a maximum amount of strain in the gasket 65 in this region, which can easily be detected by an eddy current probe 55 such as that discussed with respect to FIGS. 4A and 4B, as the compression and consequent stretching of the gasket 65 in the area just under the head of the bolt 72 creates a localized thinning of tagged particles 66. In this particular example of the method of the invention, the intensity of these stresses is measured by first scanning the gasket 65 in an uncompressed state such as that illustrated in FIG. 6A, and then scanning the gasket in the compressed state illustrated in FIG. 6B, and then comparing the various readings obtained from the eddy current probe 55 (by way of a microprocessor or the like) for each square area of the gasket 65 in order to determine the strain gradients present across the area of the gasket 65. In a case where the gasket 65 is being initially mounted between a compression ring 67 and the upper edge 68 of a pressurized container, the method may be coordinated with the amount of torque applied to each of the clamping bolts 72 so that a desired pattern of uniform, minimum strain is obtained across the entire area of the gasket 65. When the gasket 65 has already been mounted in place, the method may be used not only to determine whether or not there are localized regions of either too little or too much strain, but further to detect the existence of cracks or other discontinuities which could seriously impair the ability of the gasket 65 to perform its sealing function.

We claim:

1. A method for determining a thickness of a structure formed of non-electrically conductive material that is adjacent to a second material that is both non-electrically conductive and nonferromagnetic by means of an eddy current probe that electromagnetically couples with ferromagnetic material, said coupling being characterized by a magnitude, comprising the steps of:
   uniformly dispersing a tagging substance in the first non-conductive material to a selected density, wherein said tagging substance consists predominantly of finely divided particulate ferromagnetic material from iron lignosulfonate to tag the material forming said structure;
   calibrating said eddy current probe with a non-electrically conductive sample material having a known thickness that has been tagged with the same type of particulate ferromagnetic material at the same density by measuring the magnitude of the electromagnetic coupling at said known thickness, and
   scanning said eddy current probe over said structure, and
   determining the thickness of said structure by comparing the magnitude of the electromagnetic coupling between said probe and said structural material with the magnitude of said electromagnetic coupling with said sample material.

2. A method as defined in claim 1, wherein said ferromagnetic material comprises between about 1 to 3% by weight of said non-conductive structure.

3. A method as defined in claim 1, wherein said non conductive structure is made from a hardenable, fluent material, and wherein said ferromagnetic material is uniformly dispersed throughout said structure by admixing a colloidal suspension of said particles with the fluent material prior to hardening of said fluent material into said structure.

4. A method as defined in claim 3, wherein said colloidal suspension of said ferromagnetic particles is an aqueous colloidal solution of ferromagnetic iron lignosulfonate.

5. A method as defined in claim 1, wherein said sample material is a portion of said non-conductive structure having a known thickness.

6. A method as defined in claim 1, wherein said non-conductive material is a moldable organic material, and said step of uniformly dispersing finely divided particulate material in said non-conductive material is implemented by thoroughly mixing a colloidal solution of ferromagnetic iron lignosulfonate with said moldable organic material when said material is in a liquid state.

7. A method as defined in claim 1, wherein said non-conductive material is an elastomer.

8. A method as defined in claim 1, wherein said non-conductive material is bitumen.

9. A method for determining a thickness of a structure of a non-electrically conductive material that is adjacent to another structure that is both non-electrically conductive and non-ferromagnetic by means of a probe assembly that emanates electromagnetic radiation at a plurality of different frequencies that electromagnetically couple with ferromagnetic material, said coupling being characterized by a magnitude, comprising the steps of
   uniformly dispersing finely divided particulate ferromagnetic material from iron lignosulfonate in the non-electrically conductive material forming the structure to a selected density to tag said structure;
   calibrating said probe assembly with a non-electrically conductive sample material having a known thickness that has been tagged with said particulate ferromagnetic material at said selected density by measuring the magnitude of the coupling between electromagnetic radiation emanated from the probe assembly and the sample material;
   scanning said probe assembly over said structure while said probe emanates said radiation, and
   determining the thickness of said structure by comparing the magnitude of the electromagnetic coupling between the electromagnetic radiation emanated by said probe assembly and said sample material with the magnitude of the electromagnetic coupling between said electromagnetic radiation and said non-conducting structure.

* * * * *